(12) United States Patent
Kowarschik et al.

(10) Patent No.: US 11,080,899 B2
(45) Date of Patent: Aug. 3, 2021

(54) METHOD FOR THREE-DIMENSIONAL DIGITAL SUBTRACTION ANGIOGRAPHY AND APPARATUS

(71) Applicant: Siemens Healthcare GmbH, Erlangen (DE)

(72) Inventors: Markus Kowarschik, Nuremberg (DE); Michael Manhart, Fürth (DE)

(73) Assignee: Siemens Healthcare GmbH, Erlangen (DE)

(*) Notice: Subject to any disclaimer, the term of this patent is extended or adjusted under 35 U.S.C. 154(b) by 97 days.

(21) Appl. No.: 16/547,188

(22) Filed: Aug. 21, 2019

(65) Prior Publication Data
US 2020/0074700 A1    Mar. 5, 2020

(30) Foreign Application Priority Data
Aug. 31, 2018 (EP) .................... 18191913

(51) Int. Cl.
*G06T 11/00* (2006.01)
*G06T 5/50* (2006.01)
(Continued)

(52) U.S. Cl.
CPC .......... *G06T 11/008* (2013.01); *G06T 3/0068* (2013.01); *G06T 5/50* (2013.01);
(Continued)

(58) Field of Classification Search
CPC ......... G06T 11/003–008; G06T 3/0068–0081; G06T 5/50; G06T 7/0012;
(Continued)

(56) References Cited

U.S. PATENT DOCUMENTS 5,839,440 A    11/1998  Liou
7,505,549 B2*  3/2009  Ohishi .................. A61B 6/469
                                                    378/4
(Continued)

OTHER PUBLICATIONS

Unberath, Mathias et al., "Prior-Free Respiratory Motion Estimation in Rotational Angiography", Feb. 2018, IEEE, vol. 37 Issue 9, pp. 1999-2009 (Year: 2018).*

(Continued)

*Primary Examiner* — Vu Le
*Assistant Examiner* — Julius Chenjun Chai
(74) *Attorney, Agent, or Firm* — Lempia Summerfield Katz LLC

(57) ABSTRACT

A method is provided for producing a high-resolution three-dimensional digital subtraction angiography image of an examination object. The method includes: providing or recording of a data set of a three-dimensional rotational run of an imaging system around the examination object without administration of contrast agent (e.g., mask run); motion compensation of the data set of the mask run by a method based on the epipolar consistency conditions; providing or recording of a data set of a three-dimensional rotational run of the imaging system around the examination object with administration of contrast agent (e.g., fill run); motion compensation of the data set of the fill run by a method based on the epipolar consistency conditions; reconstructing a first volume from the compensated data set of the mask run (e.g., mask volume) and a second volume from the compensated data set of the fill run (e.g., fill volume); rigid 3D-3D registration of the first volume and second volume relative to one another; and calculating a high-resolution three-dimensional digital subtraction angiography image by subtracting the mask volume from the fill volume.

11 Claims, 2 Drawing Sheets

(51) Int. Cl.
G06T 3/00 (2006.01)
G06T 7/00 (2017.01)

(52) U.S. Cl.
CPC .. G06T 7/0012 (2013.01); *G06T 2207/10081* (2013.01); *G06T 2207/30101* (2013.01); *G06T 2211/404* (2013.01)

(58) Field of Classification Search
CPC . G06T 2207/10081; G06T 2207/30101; G06T 2211/40–404; A61B 6/504
See application file for complete search history.

(56) References Cited

U.S. PATENT DOCUMENTS

| | | | | |
|---|---|---|---|---|
| 10,682,110 | B2* | 6/2020 | Leghissa | G01R 33/4812 |
| 2008/0085034 | A1* | 4/2008 | Hildebrandt | A61B 90/36 |
| | | | | 382/107 |
| 2012/0201439 | A1* | 8/2012 | Rauch | G06T 7/20 |
| | | | | 382/130 |
| 2014/0016844 | A1* | 1/2014 | Afanasenko | G06T 5/50 |
| | | | | 382/130 |
| 2017/0345145 | A1* | 11/2017 | Nempont | G06T 7/246 |
| 2017/0347982 | A1* | 12/2017 | Rouet | A61B 6/481 |

OTHER PUBLICATIONS

Wagner, Martin et al. "Feasibility of intra-acquisition motion correction for 4D DSA reconstruction for applications in the thorax and abdomen", Mar. 2018, SPIE Medical Imaging, vol. 10574 (Year: 2018).*

Bruder, H., et al. "Compensation of skull motion and breathing motion in CT using data-based and image-based metrics, respectively." Medical Imaging 2016: Physics of Medical Imaging. vol. 9783. International Society for Optics and Photonics, 2016. pp. 1-12.

Frysch, Robert, and Georg Rose. "Rigid motion compensation in interventional C-arm CT using consistency measure on projection data." International Conference on Medical Image Computing and Computer-Assisted Intervention. Springer, Cham, 2015. pp. 298-306.

Rohkohl, Christopher, et al. "Interventional 4-D motion estimation and reconstruction of cardiac vasculature without motion periodicity assumption." International Conference on Medical Image Computing and Computer-Assisted Intervention. Springer, Berlin, Heidelberg, 2009. pp. 1-8.

Viola, Paul, and William M. Wells III. "Alignment by maximization of mutual information." International journal of computer vision 24.2 (1997): pp. 1-29.

Wagner, Martin, et al. "Feasibility of intra-acquisition motion correction for 4D DSA reconstruction for applications in the thorax and abdomen." Medical Imaging 2018: Image Processing. vol. 10574. International Society for Optics and Photonics, 2018, pp. 1-8.

European Search Report for European Patent Application No. 18191913.5-1124 dated Mar. 6, 2019.

* cited by examiner

METHOD FOR THREE-DIMENSIONAL DIGITAL SUBTRACTION ANGIOGRAPHY AND APPARATUS

The present patent document claims the benefit of European Patent Application No. 18191913.5, filed Aug. 31, 2018, which is also hereby incorporated by reference.

TECHNICAL FIELD

The disclosure relates to a method for producing a high-resolution three-dimensional digital subtraction angiography image of an examination object as well as an apparatus for performing the method.

BACKGROUND

"Simple" digital subtraction angiography (DSA) is used for the examination of blood vessels. In this procedure, multiple temporally successive x-ray images of a body part to be examined, (e.g., a brain), are produced while a contrast agent is being injected. This results in one x-ray image without contrast agent, (also known as the mask image), and further x-ray images with a distribution of contrast agent. The digital mask image is subtracted from the subsequent x-ray images. What remain are the parts that differ, e.g., the blood vessels.

3D digital subtraction angiography (3D DSA) allows a high-resolution representation, e.g., of contrast-enhanced cerebral vessels as 3D volumes. A protocol including, for example, 5s DynaCT mask run, 5s return run, and 5s DynaCT fill run may be used for this purpose. Here, the two-dimensional x-ray projections may originate from a scanning protocol of a C-arm x-ray device (e.g., DynaCT) rotating around the body part. The comparatively long recording time means there is an increased likelihood of patient movements during and between the DynaCTs.

The mask images may be subtracted from the fill images, and the subtracted images reconstructed to form a 3D volume. For the purpose of motion compensation, a 2D/2D registration between the individual mask images and fill images is then used. One problem with this approach is that 3D movements in the 2D x-ray images may only be estimated and compensated for to a limited extent.

SUMMARY AND DESCRIPTION

The scope of the present disclosure is defined solely by the appended claims and is not affected to any degree by the statements within this summary. The present embodiments may obviate one or more of the drawbacks or limitations in the related art.

An object of the present disclosure is to provide a method for producing a high-resolution three-dimensional digital subtraction angiography image of an examination object, which allows for improved motion compensation. In addition, an object of the disclosure is to provide an x-ray device suitable for performing the method.

The object is achieved by a method for producing a high-resolution three-dimensional digital subtraction angiography image of an examination object and by an apparatus.

The method for producing a high-resolution three-dimensional digital subtraction angiography image of an examination object includes: providing or recording of a data set of a three-dimensional rotational run of an imaging system around the examination object without administration of contrast agent (e.g., mask run); motion compensation of the data set of the mask run by a method based on the epipolar consistency conditions; providing or recording of a data set of a three-dimensional rotational run of the imaging system around the examination object with administration of contrast agent (e.g., fill run); motion compensation of the data set of the fill run by a method based on the epipolar consistency conditions; reconstructing a first volume from the compensated data set of the mask run (e.g., mask volume) and a second volume from the compensated data set of the fill run (e.g., fill volume); rigid 3D-3D registration of the first volume and second volume relative to one another; and calculating a high-resolution three-dimensional digital subtraction angiography image by subtracting the mask volume from the fill volume. By the method, patient movements may be eliminated particularly effectively both during a certain rotational run and also between two different rotational runs (e.g., mask run and fill run) so that a very high-quality, error-minimized 3D digital subtraction angiography image of vessels or a vascular tree, (e.g., from the brain or heart of a patient), is produced. The use of motion compensation based on the epipolar consistency conditions for each rotational run allows the movements occurring during the rotational run to be compensated for. Both volumes are then reconstructed individually and rigidly registered to one another. This allows movements occurring between the rotational runs to be compensated for. The high quality of the volume images allows for particularly thorough diagnoses to be made, which contributes to improved medical care for the patient.

The rotational runs may be performed with C-arm x-ray devices in cone-beam geometry (e.g., cone beam CT runs or DynaCT runs). As the C-arm rotates around the examination object, a plurality of projection images are recorded at different angles of rotation. A rotational run may y include a rotation of at least 200° (or 180°+ opening angle).

A computationally efficient rigid motion compensation during individual C-arm rotational runs may be achieved by a method based on the epipolar consistency conditions (ECC). Motion compensation of this type is known, e.g., from the article "Rigid Motion Compensation in Interventional C-arm CT Using Consistency Measure on Projection Data" by R. Frysch and G. Rose, International Conference on Medical Image Computing and Computer-Assisted Intervention, Springer, Cham, 2015, pp. 298-306. Epipolar geometry is used in order to identify redundancies in projection images. The epipolar consistency conditions are particularly robust consistency parameters that determine redundancies from the whole projection data set, based on Grangeat's known fundamental algorithm for cone-beam CT.

According to one embodiment, the method is performed during a scanning protocol initially with one mask run followed by at least one fill run, e.g., in combination with the live recording of all x-ray image data. A further return run may be integrated between the mask run and fill run in order that the C-arm may start again from the same position in the fill run as in the mask run. By way of example, a protocol consisting of, e.g., 5s DynaCT mask run, 5s return run, and 5s DynaCT fill run may be used.

According to a further embodiment, the ECC motion compensation of the data set of the mask run is performed directly after the recording of the mask run. This allows the method to be performed in a particularly time-saving manner. Depending on the duration of the motion compensation, it is therefore performed at least partially during the recording of the fill run, and if there is a return run, also during the return run. A reconstruction of the mask volume may also be performed as soon as the motion-compensated data set of the mask run is available. The data set of the fill run is motion-compensated after it has been recorded and is then reconstructed to form the fill volume.

Alternatively, previously recorded and stored data sets with a mask run and at least one fill run may be retrieved from a storage unit or data library and used for the method.

According to a further embodiment, redundancies between the data sets for different rotational runs are additionally used to perform motion compensation between the rotational runs. The background to this is that, particularly with intravenous injections, contrast-agent-related inconsistencies between the projection images in the case of a mask run and the projection images in the case of a fill run are small in comparison with patient-motion-related inconsistencies and may be disregarded. Consequently, additional redundancies between the projection images of the different rotational runs, (e.g., between the mask run and a fill run), may be used to achieve an improved compensation for both in-plane movements during a rotation, as well as movements between the rotational runs.

The disclosure further includes a C-arm x-ray device having an imaging system with a C-arm, on which an x-ray source and an x-ray detector are mounted and which is designed for a rotational movement around an examination object and for recording a large number of projection images during the rotational movement, a computing unit for processing data sets for motion compensation of the data set of the mask run by a method based on the epipolar consistency conditions, for the reconstruction of the compensated data set, for the rigid 3D-3D registration of reconstructed volumes, and for the calculation of three-dimensional digital subtraction angiography images, a system controller for actuating the x-ray device, and a display unit for displaying the calculated DSA.

BRIEF DESCRIPTION OF THE DRAWINGS

Advantageous embodiments of the disclosure are explained in greater detail below in the drawings, without thereby limiting the disclosure to these exemplary embodiments. In the drawings.

DETAILED DESCRIPTION

Figure 1:
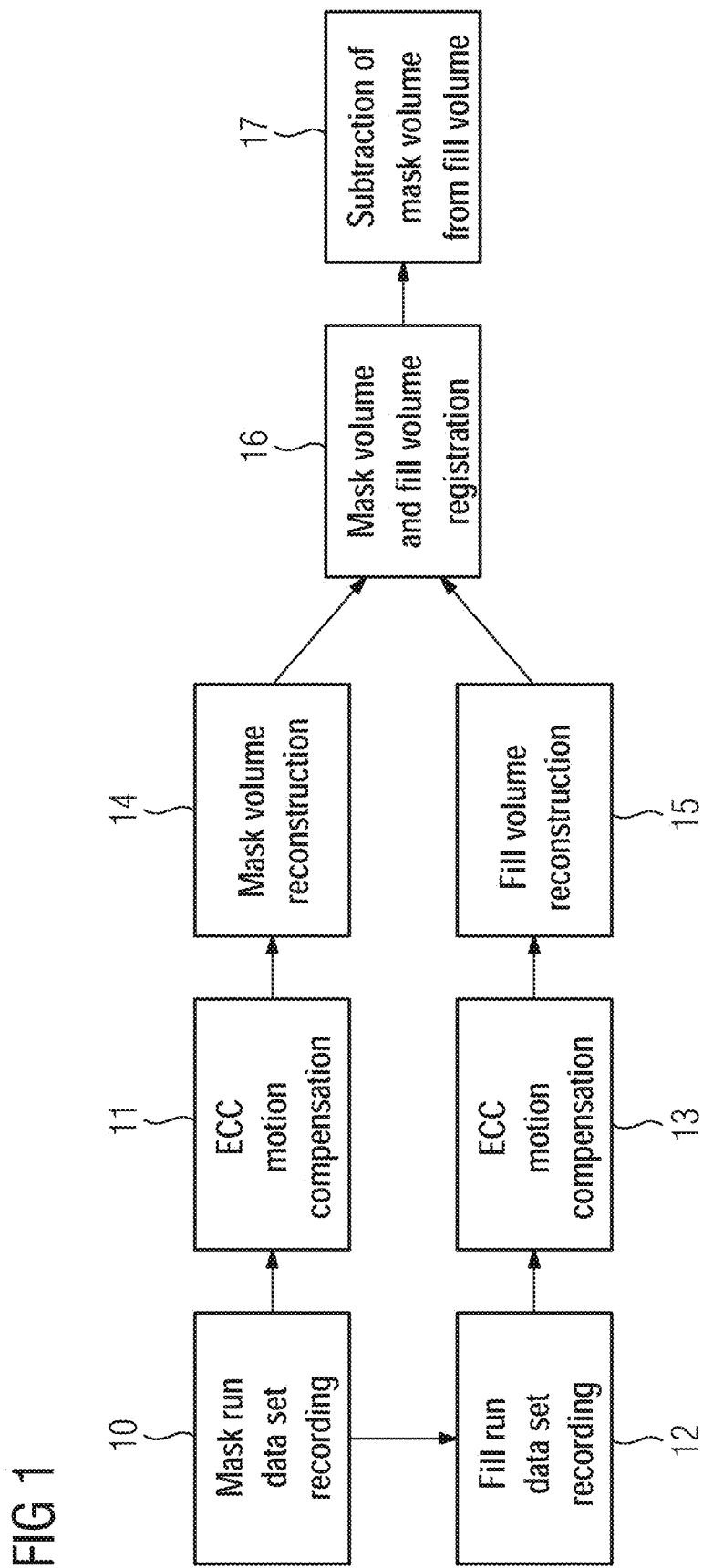
FIG. 1 depicts an example of a sequence of a method for producing a 3D DSA.

FIG. 1 depicts a sequence of a method for digital 3D subtraction angiography, in which both the data set for the mask run and the data set for the fill run are recorded directly. Alternatively, the data sets may also be retrieved from a storage unit or data library after having previously been recorded and stored.

Digital 3D subtraction angiography (3D DSA) allows a high-resolution representation of contrast-enhanced vascular trees, e.g. cerebral vessels or coronary vessels, as 3D volumes.

Figure 2:
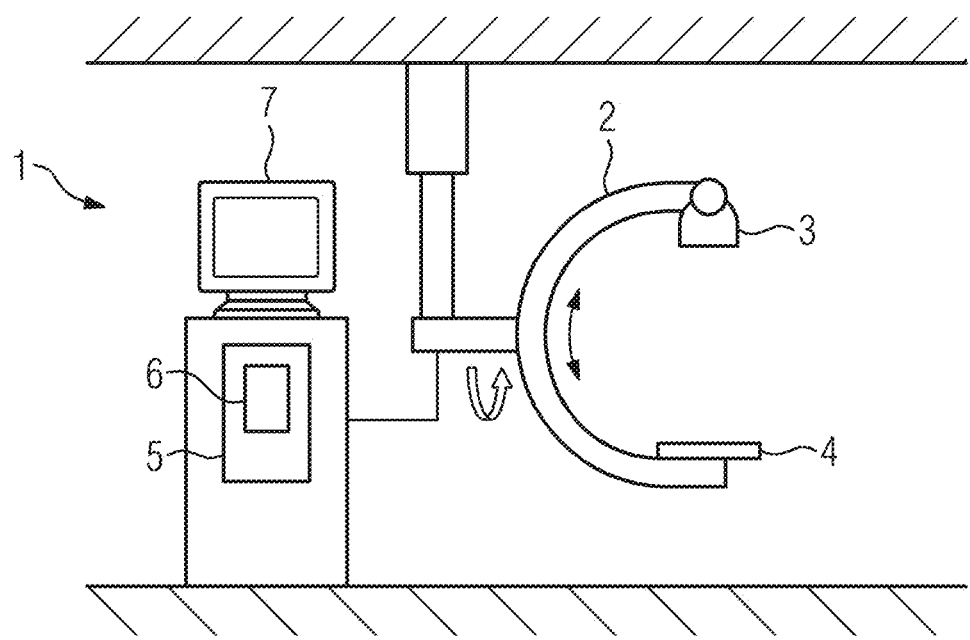
FIG. 2 depicts a view of an example of C-arm x-ray device for performing a method as disclosed herein.

In act 10, using a C-arm x-ray device having an imaging system with a C-arm and designed for recording three-dimensional x-ray images, a data set is recorded during a three-dimensional rotational run of the imaging system around an examination object without administration of contrast agent (e.g., mask run). An exemplary C-arm x-ray device 1 is depicted in FIG. 2. An x-ray source 3 and a planar x-ray detector 4 are arranged on the C-arm 2 and the C-arm 2 is configured such that it may perform a rotational movement around the examination object while recording a large number of projection images from different projection directions. This type of imaging with subsequent reconstruction is referred to, e.g., as cone-beam CT or also as DynaCT. The C-arm x-ray device is actuated by a control unit 5.

The recorded data set of the mask run is motion-compensated in act 11 by a method based on the epipolar consistency conditions (ECC). A computationally efficient rigid motion compensation during individual C-arm rotational runs (e.g., cone-beam CT runs or DynaCT runs) may be achieved by a method of this type. Motion compensation of this type is known, e.g., from the article "Rigid Motion Compensation in Interventional C-arm CT Using Consistency Measure on Projection Data" by R. Frysch and G. Rose, International Conference on Medical Image Computing and Computer-Assisted Intervention, Springer, Cham, 2015, pp. 298-306. Epipolar geometry is used here in order to identify redundancies in projection images. The epipolar consistency conditions are particularly robust consistency parameters that determine redundancies from the whole projection data set, based on Grangeat's known fundamental algorithm for cone-beam CT. For this purpose, redundant line integrals between the projection images are identified with the aid of projective geometry. The geometry is adjusted in an iterative method such that an error metric is optimized with respect to these redundancies. In this way, this method based purely on projection images enables a particularly computationally efficient estimation of rigid patterns of movement.

In act 12, a data set is recorded using the same C-arm x-ray device during a three-dimensional rotational run of the imaging system around the examination object with administration of contrast agent (e.g., fill run). The rotational run may not differ as such from the mask run in terms of duration, angle covered, and number of projection images. A contrast agent, however, is injected into the patient's vessels to be examined before the fill run is performed.

The recorded data set of the fill run is motion-compensated in act 13 by the same method based on the epipolar consistency conditions, as with the data set of the mask run. The motion compensation of the data sets is performed for example by a calculation unit 6 of the C-arm x-ray device.

A scanning protocol consisting of mask run, return run and fill run may be used to produce 3D DSA. A scanning protocol of this type may be performed in the present method. The duration of each run may be a few seconds, and so the scanning protocol may include, for example, 5s DynaCT mask run, 5s return run, and 5s DynaCT fill run. In the method used, the motion compensation of the mask run may be performed partially during the return run and/or the fill run. This allows the method to be performed particularly quickly.

Once the motion-compensated data set of the mask run is available, it is reconstructed in act 14 to form a volume (e.g., mask volume). Likewise, once the motion-compensated data set of the fill run is available, in act 15, it is reconstructed to form a volume (e.g., fill volume). Known reconstruction algorithms are used for the reconstructions; the reconstructions may be performed, e.g., by the calculation unit 6 of the C-arm x-ray device.

The sequence of the method is not necessarily stipulated. Although the mask run may take place before the fill run (see, e.g., scanning protocol), it is also possible for the motion compensation of the mask run to be performed only after the fill run, before the motion compensation of the fill run, simultaneously therewith, or thereafter. The sequence of the reconstructions of the motion-compensated data sets of the mask run and fill run may also be varied as required. More than one fill run may also be performed if necessary. In such a case, all fill runs are motion-compensated accordingly and reconstructed to form fill volumes.

When both the mask volume and the fill volume are available, in act 16 a rigid registration of both volumes to one another is performed. For this purpose, a method such as, e.g., that described in the article by Paul Viola et al.: Alignment by Maximization of Mutual Information; Int. Journal of Computer Vision, 24 (2) pp. 137-154, 1997, may be used. The rigid registration of the volumes to one another compensates for a movement of the examination object between the mask run and fill run.

In act 17, a three-dimensional digital subtraction angiography image is then calculated by subtracting the mask volume from the fill volume. This subtraction may also be performed by the calculation unit 6. The 3D DSA may be displayed on a display unit 7 of the C-arm x-ray device.

Furthermore, at a suitable point in the method, additional redundancies between the projection images of the different rotational runs, e.g. between the mask run and the fill run, may be used to achieve an improved compensation for movements of the patient both during and between the rotational runs.

The method proposed enables computationally efficient rigid 3D motion compensation of the examination object (e.g., of a vascular tree of a patient's head or heart) both during and between the rotational runs for recording data sets for 3D DSA.

In summary, the disclosure relates to a method for producing a high-resolution three-dimensional digital subtraction angiography image of an examination object. The method includes: providing or recording of a data set of a three-dimensional rotational run of an imaging system around the examination object without administration of contrast agent (e.g., mask run); motion compensation of the data set of the mask run by a method based on the epipolar consistency conditions; providing or recording of a data set of a three-dimensional rotational run of the imaging system around the examination object with administration of contrast agent (e.g., fill run); motion compensation of the data set of the fill run by a method based on the epipolar consistency conditions; reconstructing a first volume from the compensated data set of the mask run (e.g., mask volume) and a second volume from the compensated data set of the fill run (e.g., fill volume); rigid 3D-3D registration of the first volume and second volume relative to one another; and calculating a high-resolution three-dimensional digital subtraction angiography image by subtracting the mask volume from the fill volume. The disclosure further includes a C-arm x-ray device for performing the method.

Although the disclosure was illustrated and described in more detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for producing a high-resolution three-dimensional digital subtraction angiography image of an examination object, the method comprising:
providing or recording of a data set of a three-dimensional rotational mask run of an imaging system around the examination object without administration of a contrast agent;
compensating for motion of the data set of the mask run based on epipolar consistency conditions;
providing or recording of a data set of a three-dimensional rotational fill run of the imaging system around the examination object with administration of the contrast agent;
compensating for motion of the data set of the fill run based on the epipolar consistency conditions;
reconstructing a mask volume from the compensated data set of the mask run and a fill volume from the compensated data set of the fill run;
performing a rigid 3D-3D registration of the mask volume and the fill volume relative to one another; and
calculating a high-resolution three-dimensional digital subtraction angiography image by subtracting the mask volume from the fill volume,
wherein redundancies between the data set of the mask run and the data set of the fill run are additionally used to perform motion compensation between and/or during the mask run and the fill run.

2. The method of claim 1, wherein the method is performed during a scanning protocol initially with one mask run followed by at least one fill run.

3. The method of claim 2, wherein the motion compensation of the data set of the mask run is performed directly after the recording of the mask run.

4. The method of claim 2, wherein the motion compensation of the data set of the mask run is performed during the recording of the fill run.

5. The method of claim 1, wherein the motion compensation of the data set of the mask run is performed directly after the recording of the mask run.

6. The method of claim 5, wherein the compensation for motion of the data set of the mask run or the fill run based on the epipolar consistency conditions first identifies, by the epipolar consistency conditions, redundancies in projection planes in a large number of projection images of the mask run or the fill run and uses these for motion compensation of the examination object during the respective mask run or the fill run.

7. The method of claim 1, wherein the motion compensation of the data set of the mask run is performed during the recording of the fill run.

8. The method of claim 7, wherein the compensation for motion of the data set of the mask run or the fill run based on the epipolar consistency conditions first identifies, by the epipolar consistency conditions, redundancies in projection planes in a large number of projection images of the mask run or the fill run and uses these for motion compensation of the examination object during the respective mask run or the fill run.

9. The method of claim 1, wherein the data set of the mask run and the data set of the fill run are retrieved from a data storage unit.

10. The method of claim 1, wherein the compensation for motion of the data set of the mask run or the fill run based on the epipolar consistency conditions first identifies, by the epipolar consistency conditions, redundancies in projection planes in a large number of projection images of the mask run or the fill run and uses these for motion compensation of the examination object during the respective mask run or the fill run.

11. A C-arm x-ray device comprising:
an imaging system with a C-arm, on which an x-ray source and an x-ray detector are mounted;
a system controller for actuating the imaging system; and
a display,
wherein the imaging system is configured for a rotational movement around an examination object and for recording a plurality of projection images during the rotational movement, wherein the imaging system is configured to record a data set of a three-dimensional rotational mask run around the examination object without administration of a contrast agent, and wherein the imaging system is configured to record a data set of a three-dimensional rotational fill run around the examination object with administration of the contrast agent,
wherein the C-arm x-ray device is configured to: compensate for motion of the data set of the mask run based on epipolar consistency conditions, compensate for motion of the data set of the fill run based on the epipolar consistency conditions, reconstruct a mask volume from the compensated data set of the mask run, reconstruct a fill volume from the compensated data set of the fill run, perform a rigid 3D-3D registration of the mask volume and the fill volume relative to one another, and calculate a three-dimensional digital subtraction angiography image by subtracting the mask volume from the fill volume,
wherein redundancies between the data set of the mask run and the data set of the fill run are additionally used to perform motion compensation between and/or during the mask run and the fill run, and
wherein the display is configured to display the calculated three-dimensional digital subtraction angiography image.

* * * * *